United States Patent [19]

Siragusa

[11] Patent Number: 4,940,454
[45] Date of Patent: Jul. 10, 1990

[54] HYGIENIC SWAB-TYPE DEVICE WITH EXTENDER HANDLE COVER

[76] Inventor: Angela Siragusa, 1645 Overing St., Bronx, N.Y. 10461

[21] Appl. No.: 299,270

[22] Filed: Jan. 23, 1989

[51] Int. Cl.$^5$ .............................................. A61M 35/00
[52] U.S. Cl. ........................................ 604/1; 294/116; 294/131; 606/207
[58] Field of Search ................. 294/116, 131; 15/145, 15/150, 210 A; 604/1, 11; 128/321, 354; 606/106, 136, 157, 205, 210

[56] References Cited

U.S. PATENT DOCUMENTS

| | | | |
|---|---|---|---|
| 331,363 | 12/1885 | Wyatt | 294/131 |
| 2,014,807 | 9/1935 | Keyzer | 294/116 |
| 2,224,384 | 12/1940 | Gratiot | 128/354 |
| 2,366,982 | 1/1945 | Pryor | 294/116 |
| 2,514,481 | 7/1950 | Ellinger | 15/145 |
| 2,571,906 | 10/1951 | Love | 15/210 |
| 3,093,402 | 6/1963 | Sisson | 294/116 |
| 3,646,939 | 3/1972 | Sklar | 128/321 |
| 3,724,463 | 4/1973 | Vail | 604/1 |
| 3,777,760 | 12/1973 | Essner | 604/1 |
| 3,818,911 | 6/1974 | Fournier | 604/1 |
| 4,152,804 | 5/1979 | Morris | 15/184 |
| 4,676,773 | 6/1987 | Sheldon | 604/11 |
| 4,753,235 | 6/1988 | Hasson | 128/321 |
| 4,815,460 | 3/1989 | Porat et al. | 128/321 |
| 4,836,596 | 6/1989 | Owen | 128/354 |

FOREIGN PATENT DOCUMENTS 0297703 6/1932 Italy ..................... 294/131

Primary Examiner—John D. Yasko
Assistant Examiner—Adam J. Cermak
Attorney, Agent, or Firm—Lackenbach, Siegel, Marzullo & Aronson

[57] ABSTRACT

A hygienic swab-type device usable for cleansing or as a medical applicator is provided by compact tongs with a cover which functions as a scabbard or housing when the tongs are not in use and in use as a handle extension for the tongs. The tongs are pivotally connected and have clamping end portions for clamping and holding a replaceable or disposable hygienic swab for cleansing or treating of the body such as rectal and vaginal areas. The cover is made of a rigid material and has a pocket formed therein into which the operating ends of the tongs are insertable longitudinally in use effectively holding the tongs in a closed position and extending longitudinally therefrom. The cover accordingly provides a longitudinal handle extension for the tongs inserted into the pocket and ease of manipulation for access to the body areas to be cleansed or treated with the hygienic swab.

14 Claims, 2 Drawing Sheets

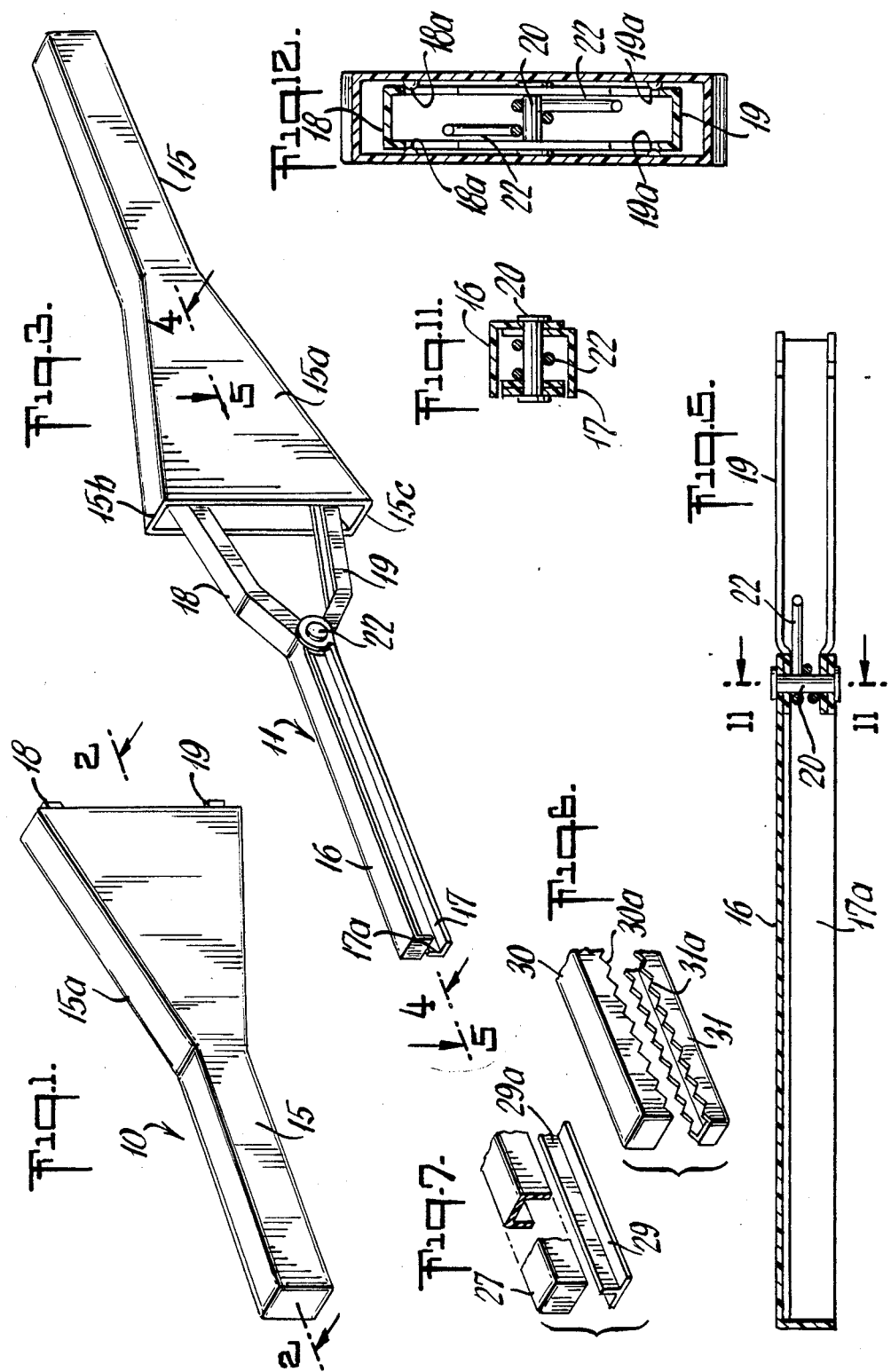

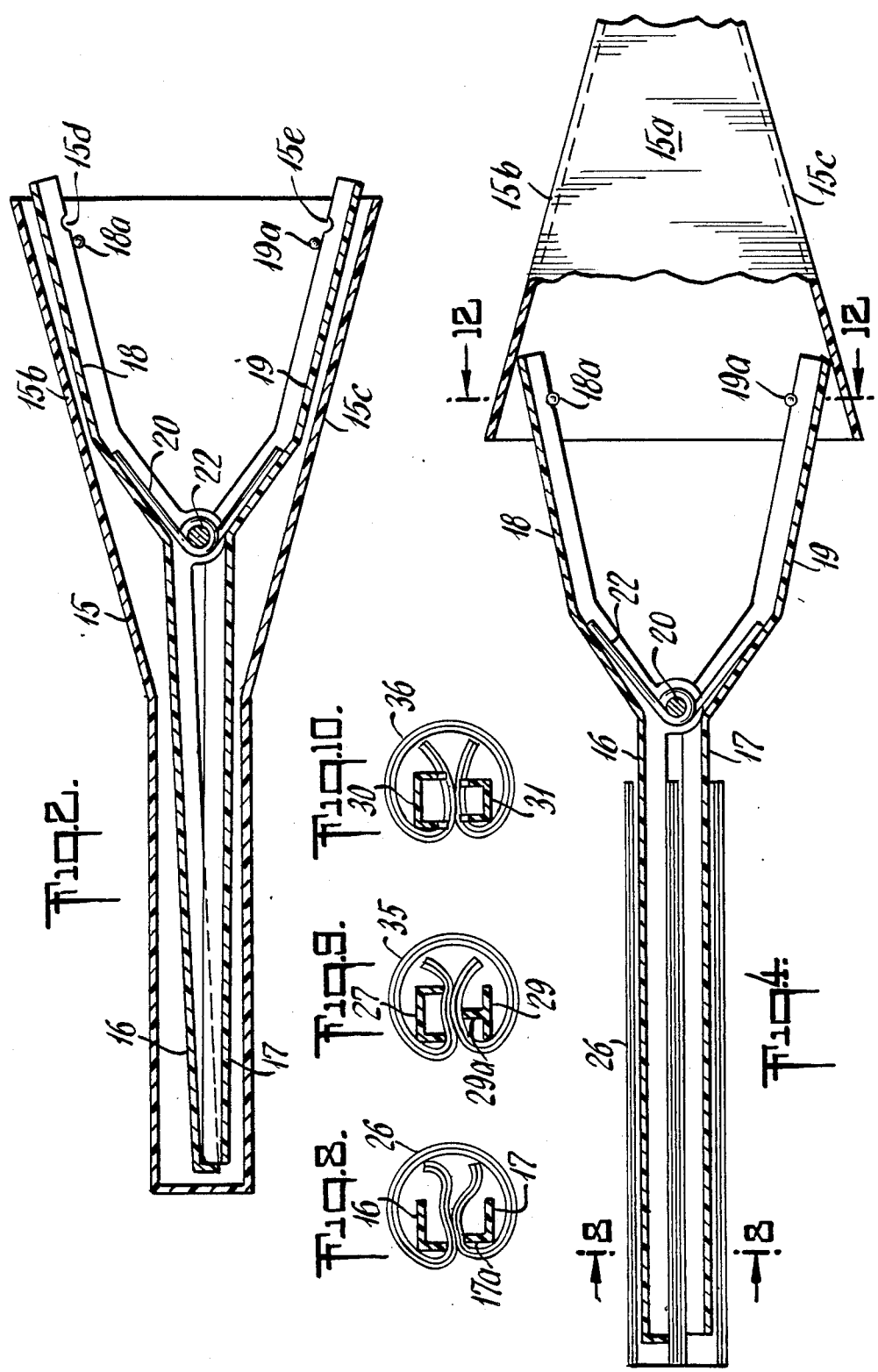

HYGIENIC SWAB-TYPE DEVICE WITH EXTENDER HANDLE COVER

BACKGROUND OF THE INVENTION

FIELD OF THE INVENTION

This invention relates generally to hygienic devices and more particularly to a hygienic swab-type device.

Hygienic vaginal swab devices for use in cleansing the vaginal canal are known. Known devices have an elongated manually rotatable element having a series of adjacent spiral coils of absorbent strands wound thereon. Such a device is disclosed in U.S. Pat. No. 3,724,463.

Surgical instruments such as surgical sticks used for handling absorbent sponges, gauze or the like are likewise known. Such sticks hold absorbent material locked between jaws thereof and can be sterilized and packaged so that it is ready for use by a surgeon or one having to use a surgical swab. An example of such a device is disclosed in U.S. Pat. No. 3,777,760.

Tongs for the manipulation of clothes are well known in the art and are used for lifting and manipulating swabs and absorbent materials when being used or sterilized. The use of these cleansing devices with swabs are limited in that they are constructed for use by individuals which have normal appendages and are not circumscribed in their movements by physical limitations. Generally known hygienic devices cannot be readily manipulated by those that are unable to readily reach areas of their body to be cleansed by themselves.

SUMMARY OF THE INVENTION

It is an object of the present invention to provide a hygienic swab-type device which is compact and can be assembled into an extended cleansing instrument for ease of manipulation of a hygienic swab.

Another object of the present invention is to provide a hygienic swab-type device of simple construction, readily stowed and assembled.

The hygienic swab-type device according to the invention has a pair of pivotally connected tongs pivotally operable for clamping and holding a hygienic replaceable or disposable swab for cleansing of the body such as rectal and vaginal areas. The tongs have elongate clamping end portions normally in a closed position. The tongs are manually operable from a normally closed position to an open position for mounting and releasably holding the hygienic swab.

A cover made of a rigid material is provided for housing the tongs when not in use. The cover defines a pocket into which the tongs are partially insertable longitudinally with operating end portions thereof effectively held so that the tongs are maintained in the closed position. The cover provides a longitudinal handle extension for the tongs for ease of access to the body areas to be cleansed with a disposable hygienic swab manipulated with the hygienic device.

BRIEF DESCRIPTION OF THE DRAWINGS

The hygienic swab-type device according to the invention and objects thereof will be better understood from the following description, appended claims and drawings in which:

FIG. 1, is a perspective side elevation view of the hygienic device and cover thereof according to the invention;

FIG. 2, is a longitudinal section view taken along section line 2—2 of FIG. 1;

FIG. 3, is a perspective view of the hygienic device in FIG. 1 illustrated in assembly for use;

FIG. 4, is a section view taken along section line 4—4 of FIG. 3 illustrating the hygienic device in assembly for use;

FIG. 5, is a section view taken along section line 5—5 of FIG. 3;

FIGS. 6 and 7, are fragmentary perspective views, partly in section, illustrating different embodiments of elongate clamping end portions of the tongs;

FIGS. 8, 9 and 10, are all cross section views of embodiments of the tongs with a disposable swab thereon, with section line 8—8 shown in FIG. 4;

FIG. 11, is a section view taken along section line 11—11 of FIG. 5; and

FIG. 12, is a section view taken along section line 12—12 of FIG. 4.

DESCRIPTION OF THE PREFERRED EMBODIMENTS

As illustrated in the drawings a hygienic swab-type device 10, according to the invention, comprises pivotally connected tongs 11 which are received and housed in a cover 15 made of a rigid material. The tongs are provided with elongate clamping end portions 16, 17, and operating end portions 18, 19 biased into a spaced apart position by a spring 20 on a pivot 22 intermediate the elongate clamping end portions 16, 17 and the operating end portions 18, 19. When not in use, the tongs 11 are housed in the cover 15 as shown in FIG. 2.

The spring 20 biases the elongate clamping end portions 16, 17 toward each other to a normally closed position in which the operating end portions 18, 19 are biased apart. The elongate clamping end portions 16, 17 are opened by operating or pressing manually the operating end portions 18, 19 toward each other so that the tongs are opened for receiving a cleansing swab 26 as illustrated in FIG. 4. The swab 26 can be either a tissue which is replaceable and disposable or may be a cloth which can be sanitized and replaced.

The clamping end portions 16, 17 are constructed as a channel and L-shaped in cross section. An upstanding part 17a fits into the U-shaped channel elongate clamping end portion 16. The clamping end portions may be constructed as illustrated in FIGS. 6 and 7 in which the clamping end portions are shown fragmentarily and partly in cross section. A channel shaped clamping end portion 27 receives an inverted T-shaped clamping end portion 29 which has an upstanding part 29a received in the channel of the opposed clamping end portion 27. The clamping end portions may also be constructed as two opposed U-shaped channels 30, 31 as shown in FIG. 6 with complementary serrations 30a and 31a defining jaws. In the clamped position of the tongs they hold the hygienic swabs 26, 35 and 36 wound thereon releasably clamped in the particular tong embodiments. The operating end portions 18, 19 are extensions of the corresponding clamping end portions of their respective embodiments of the tongs.

In all embodiments the tongs are inserted longitudinally into the cover 15 and a pocket 15a thereof having diverging end walls 15b, 15c in the position illustrated in FIG. 2, when not in use. When the tongs are in use, the position of the operating end portions 18, 19 is reversed in the cover and the operating end portions are partially inserted longitudinally into the pocket 15a as illustrated in FIGS. 3, 4 and 12. The pocket 15a is dimensioned as to the width and height thereof so the operating end portions 18, 19 of the tongs are received therein snugly and the cover accordingly is held in assembly with the tongs and functions as a longitudinal handle extension of the tongs in the closed or clamping position. In order to maintain the tongs inserted into and held within the pocket pairs of 15a, detents 18a, 19a are provided on the operating ends and received in detent-receiving recesses 15d, 15e on the sides of the pocket 15a so that the tongs are positively held extending longitudinally outwardly of the pocket as shown in FIG. 4. The pocket 15a accordingly makes it possible for the cover 15 to function as a handle for the tongs for ease of use in cleansing the body areas.

The cover substantially doubles the longitudinal length of the tongs as assembled therewith so that the hygienic device can be constructed compactly for storage when not in use and is provided with an extended handle extension providing for a more convenient use of the tongs in cleansing operations and manipulations thereof.

Those skilled in the art will understand that the hygienic swab is disposable or replaceable and can be made of tissue or cloth as required. Moreover, the swab can have medication thereon so that it can function for cleansing or treatment or both. The swab is accordingly also an applicator.

The longitudinal handle extension to the tongs makes it possible for handicapped users to more readily manipulate the tongs. Moreover, those who are overweight or have short arms and are not able to cleanse themselves readily in rectal and/or vaginal areas can readily do so with the hygienic device. The apparatus or hygienic device functions as a cleansing device or a medical instrument. In addition, although not shown, the cover 15 need not necessarily be entirely hollow, but may if desired, be generally solid except for a small pocket at the wide end for holding the tongs 11. With suitable detent-like projections (analogous to those of 18a and 19a may be employed with others, if desired, at the opposite end of the cover) on either side of the cover 15, so that the tongs 11 when not in use, may be held tightly to the cover 15 by a frictional grip with the end portions 16, 17 of the tongs 11 extending parallel along the long end of the cover.

I claim:

1. A hand held tong-like device comprising, pivotally connected tongs, the tongs having respective clamping end portions normally in a closed position and manually operable to an open position and having operating end portions for manually operating the tongs to said open position, biasing means continuously biasing the tongs to said closed position, a cover for housing the tongs therein when not in use, the cover forming an extended handle for said device when in use and defining a pocket into which the operating ends of the tongs are insertable effectively holding the tongs in the closed position, and the cover providing an elongated extension for the tongs when the operating ends thereof are inserted into said pocket; whereby access to body areas to be cleansed with a hygienic swab held by said tongs are facilitated, particularly for those users who are overweight, have short arms or may be otherwise handicapped.

2. The device according to claim 1, in which said cover is made of a rigid material.

3. The device according to claim 1, in which said biasing means comprises a spring, and the operating end portions and the spring being received in said pocket.

4. The device according to claim 1, in which said clamping end portions of the tongs for holding said hygienic swab are elongate for winding the hygienic swab thereon.

5. The device according to claim 4, in which said clamping end portions for holding said hygienic swab mate, one of the end portions is a U-shaped channel and the other is shaped like an upside down letter T in cross section and an upstanding part thereof fits into the U-shaped channel when in the closed position.

6. The hygienic swab according to claim 4, in which the clamping end portions for holding the hygienic swab are two coactive U-shaped channels confronting each other.

7. The device according to claim 4, in which one of said tong clamping end portions for holding the hygienic swab is a U-shaped channel and another cooperating clamping end portion is L-shaped and upstanding part thereof fits into the U-shaped channel.

8. The device according to claim 1, in which said pocket is dimensioned to receive the operating ends of the tongs snugly.

9. The device according to claim 8, in which the operating ends of the tongs each comprise a recess, and said cover having in said pocket receiving detents for mating with the recesses at the operating ends of said tongs for releasably holding the operating ends in position and in said pocket.

10. device according to claim 1, in which said operating ends are elastically constantly biased apart and including a pivot disposed between the clamping end portions for holding the swab and the operating end portions, said pocket receiving the operating end portions when the tongs are not in use and completely housed therein, and said pocket having outwardly diverging walls for receiving in use said operating ends reversed in position therein from their position in the cover when not in use.

11. A hand held tong-like device comprising, pivotally connected tongs, the tongs having respective clamping end portions normally in a closed position and manually operable to an open position and having operating end portions for manually operating the tongs to said open position, biasing means continuously biasing the tongs to said closed position, a cover for housing the tongs therein when not in use, the cover forming an extended handle for said device when in use, and defining a pocket into which the operating ends of the tongs are insertable effectively holding the tongs in the closed position and the cover providing an elongated extension for the tongs when the operating ends thereof are inserted into said pocket; the clamping end portions of the tongs are two elongate coactive U-shaped channels confronting each other for winding the hygienic swab thereon; whereby access to body areas to be cleansed with a hygienic swab held by said tongs are facilitated, particularly for those users who are overweight, have short arms or may be otherwise handicapped.

12. The device according to claim 11, in which said U-shaped channels have complementary serrations coactive as jaws on the elongate end portions.

13. A hand held tong-like device comprising, pivotally connected tongs, the tongs having respective clamping end portions normally in a closed position and manually operable to an open position and having operating end portions for manually operating the tongs to said open position, biasing means continuously biasing the tongs to said closed position, a cover for housing the tongs therein when not in use, the cover forming an extended handle for said device when in use, and defining a pocket into which the operating ends of the tongs are insertable effectively holding the tongs in the closed position, and the cover providing an elongated extension for the tongs when the operating ends thereof are inserted into said pocket; one of the clamping end portions of the tongs is a U-shaped channel and another cooperating clamping end portion is L-shaped and an upstanding part thereof fits into the U-shaped channel for winding the hygienic swab thereon; whereby access to body areas to be cleansed with a hygienic swab held by said tongs are facilitated, particularly for those users who are overweight, have short arms or may be otherwise handicapped.

14. The device according to claim 13, in which said U-shaped channels have complementary serrations coactive as jaws on the elongate end portions.

* * * * *